(12) United States Patent
Taylor et al.

(10) Patent No.: US 9,796,679 B2
(45) Date of Patent: Oct. 24, 2017

(54) TYPE 4 PREPILIN PEPTIDASE INHIBITORS AND METHODS OF USE

(71) Applicant: Trustees of Dartmouth College, Hanover, NH (US)

(72) Inventors: Ronald K. Taylor, Lebanon, NH (US); Gordon W. Gribble, Lebanon, NH (US)

(73) Assignee: TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 15/117,940

(22) PCT Filed: Feb. 9, 2015

(86) PCT No.: PCT/US2015/014987
§ 371 (c)(1),
(2) Date: Aug. 10, 2016

(87) PCT Pub. No.: WO2015/123130
PCT Pub. Date: Aug. 20, 2015

(65) Prior Publication Data
US 2016/0355481 A1  Dec. 8, 2016

Related U.S. Application Data

(60) Provisional application No. 61/938,434, filed on Feb. 11, 2014.

(51) Int. Cl.
*C07D 215/00* (2006.01)
*C07D 215/42* (2006.01)

(52) U.S. Cl.
CPC .................................. *C07D 215/42* (2013.01)

(58) Field of Classification Search
CPC .................................................... C07D 215/42
USPC ........................................................ 546/152
See application file for complete search history.

(56) References Cited

U.S. PATENT DOCUMENTS

| | | | |
|---|---|---|---|
| 5,532,374 A | 7/1996 | Lee et al. | 546/167 |
| 6,790,962 B2 | 9/2004 | Rotenberg et al. | 546/167 |
| 6,887,677 B1 | 5/2005 | Taylor et al. | 435/23 |
| 6,974,871 B2 | 12/2005 | Rotenberg | 546/167 |
| 2005/0201999 A1 | 9/2005 | Taylor et al. | 424/94.2 |
| 2013/0252881 A1 | 9/2013 | McArthur et al. | 514/2.8 |

FOREIGN PATENT DOCUMENTS

ES    WO 9805644    * 12/1998    ........... C07D 213/74

OTHER PUBLICATIONS

Sanchez-Martin, Journal of Medicinal Chemistry (2005), 48(9), 3354-3363.*
Rosa, Journal of Medicinal Chemistry (1996), 39(21), 4247-4254.*
LaPointe & Taylor "The type 4 prepilin peptidases comprise a novel family of aspartic acid proteases" J. Biol. Chem. 2000 275:1502-10.
March & Taylor "Identification of the Vibrio cholerae type 4 prepilin peptidase required for cholera toxin secretion and pilus formation" Mol. Microbiol. 1998 29:1481-1492.
Strom & Lory "Structure-function and biogenesis of the type IV pili" Ann. Rev. Microbiol. 1993 47:565-596.
Strom et al. "A single bifunctional enzyme, PilD, catalyzes cleavage and N-methylation of proteins belonging to the type IV pilin family" Proc. Natl. Acad. Sci. USA 1993 90:2404-2408.
Strom et al. "Posttranslational processing of type IV prepilin and homologs by PilD of Pseudomonas aeruginosa" Meth. Enzymol. 1994 235:527-540.
International Search Report and Written Opinion dated May 1, 2015 in PCT/US15/14987.
International Preliminary Report on Patentability dated Aug. 16, 2016 in PCT/US15/14987.

* cited by examiner

*Primary Examiner* — Nizal Chandrakumar
(74) *Attorney, Agent, or Firm* — Licata & Tyrrell P.C.

(57) ABSTRACT

Compounds for inhibiting Type 4 Prepilin Peptidases are provided as are methods of using the compounds as antibacterial agents.

2 Claims, No Drawings

TYPE 4 PREPILIN PEPTIDASE INHIBITORS AND METHODS OF USE

This patent application is the National Phase of International Application No. PCT/US2015/014987 filed Feb. 9, 2015, which claims the benefit of priority from U.S. Provisional Application Ser. No. 61/938,434 filed Feb. 11, 2014, the contents of which are incorporated herein by reference in their entireties.

This invention was made with government support under grant number AI 25096 awarded by the National Institutes of Health. The government has certain rights in the invention.

BACKGROUND

Anti-bacterial agents are developed by identifying unique targets not present in mammalian cells and then identifying a drug to exploit that difference such that the bacterial cells are killed or neutralized while mammalian cells are left intact and unaffected. The goal of successful anti-bacterial drug therapy is to limit toxicity in the patient while maximizing the ability of the drug to invade the bacterial cells and neutralize those cells as selectively as possible. The major classes of anti-bacterial drugs available today target a variety of different cellular components and functions of bacteria such as the cell wall, protein synthesis, cell metabolism, DNA synthesis, and the bacterial cell membrane. Each of these target cellular components or functions is related in some way to the disease process of bacterial infections that involves first colonization of the bacteria, invasion of host cells, production of cellular toxins or inflammatory agents, and a host response to those toxins or agents.

A fundamental process of all living cells, including bacteria, is the secretion of proteins across membranes. The majority of proteins that are secreted are synthesized as a precursor with an N-terminal signal sequence (or leader peptide) of about 16-24 amino acids in length. This leader sequence serves to promote recognition of the protein by the secretory apparatus of the cell and facilitates movement across the membrane. The leader sequence is subsequently processed by a leader peptidase to remove the sequence and allow release of the mature or active protein. Recent research has indicated that in the case of bacteria, there are several systems for secreting proteins and some of these systems have unique leader peptidases associated with their cognate secreted proteins. One of these systems is known as the type 2 secretion system which promotes extracellular secretion of bacterial factors such as toxins and colonization pili that are the hallmarks of the mechanisms that promote virulence of pathogenic bacteria. Pili mediate the binding of bacteria to host tissues and most pili are composed of a major protein subunit that polymerizes to form a pilus.

The type 2 secretion systems of most bacteria involve a type 4 pilin for pilus formation and type 4 pilin-like proteins for secretion of toxins and other factors associated with bacterial virulence and destruction of host tissue and enhancement of bacterial growth in the host. Highly related type 4 pili serve as the major colonization factors for up to 50 different gram-negative bacterial species and type 4 pilin-like proteins have been found for a growing number of gram-positive bacteria as well. Type 4 pili are composed of a polymerized structure of type 4 pilin. The pilin is synthesized as a prepilin with a leader peptide that is very different from those of typical secreted proteins. A type 4 specific leader peptidase is required to process a type 4 prepilin leader sequence to allow secretion of the mature protein. Importantly, this secretion system including the type 4 leader peptidase itself is only found in bacteria and is not present in humans or other potential hosts of infection. Furthermore, it has been shown that mutating the type 4 prepilin peptidase (TFPP) renders the bacterium avirulent (March & Taylor (1998) *Mol. Microbiol.* 29:1481-1492).

The type 4 signal peptide is highly conserved across all type 4 prepilin or prepilin-like proteins and is composed of 6 to 25 highly charged amino acids at the N-terminus followed by approximately 20 predominately hydrophobic amino acids. Cleavage occurs between the two domains immediately C-terminal of an invariant glycine and before the new N-terminal amino acid that is usually a methionine or a phenylalanine. Unlike cleavage of standard signal peptide by signal peptidase I, wherein the cleavage occurs on the periplasmic side of the inner membrane, processing by a type 4 peptidase occurs on the cytoplasmic side of the inner membrane (Strom & Lory (1993) *Ann. Rev. Microbiol.* 47:565-596). Previous mutational analysis and protease inhibitor evidence from studies of pilD of *Pseudomonas aeruginosa* and protein alignment analysis of the type 4 peptidase family suggested two pairs of cysteines in cytoplasmic domain 1, the largest cytoplasmic domain, to be involved in the protease active site of the enzyme (Strom, et al. (1993) *Proc. Natl. Acad. Sci. USA* 90:2404-2408). These data resulted in the categorization of type 4 prepilin peptidase (TFPP) family as a type of cysteine protease (Strom, et al. (1994) *Meth. Enzymol.* 235:527-540).

Using mutant constructs of TcpJ, a type 4 prepilin peptidase of *Vibrio cholerae*, residues essential for cleavage activity of the bacterial protease TFPP were identified as two aspartic acid residues (LaPointe & Taylor (2000) *J. Biol. Chem.* 275:1502-10). Screening assays to identify agents targeting these residues have been suggested (U.S. Pat. No. 6,887,677).

Dequalinium is a quaternary ammonium cation commonly available as the dichloride salt. The bromide, iodide, acetate, and undecenoate salts are known as well. Dequalinium chloride is a topical bacteriostat of use in the treatment of mouth and vaginal infections.

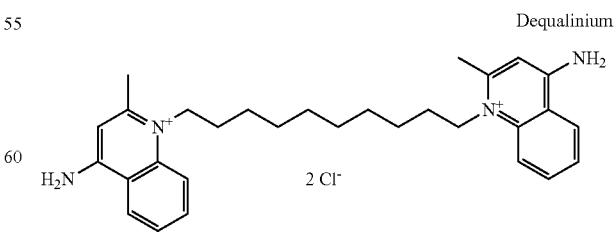

Dequalinium

Analogs of dequalinium have been described for use in inhibiting the growth of and metastasis cancer cells (U.S. Pat. No. 6,974,871 and U.S. Pat. No. 6,790,962).

SUMMARY OF THE INVENTION

This invention is a compound having the structure of Formula I:

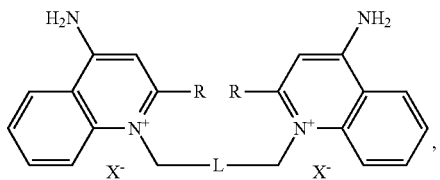

Formula I wherein R is a hydrogen, hydroxyl group or a substituted or unsubstituted $C_1$-$C_6$ alkyl group, X is an organic or inorganic anion, and L is a linker having one of the following structures:

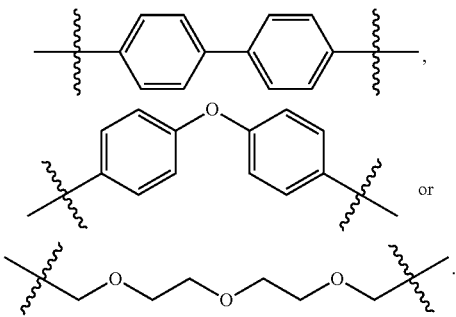

or

A pharmaceutical composition containing the compound in admixture with a pharmaceutically acceptable carrier and a method for preventing or treating a bacterial infection are also provided.

DETAILED DESCRIPTION OF THE INVENTION

It has now been demonstrated that bis-4-aminoquinolines inhibit the cleavage activity of type 4 prepilin peptidase. Inhibitors of the present invention have the structure of Formula I:

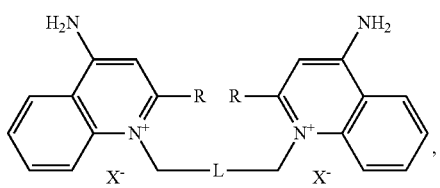

Formula I wherein R is a hydrogen, hydroxyl group or a substituted or unsubstituted $C_1$-$C_6$ alkyl group, X is an organic or inorganic anion, and L is a linker having one of the following structures.

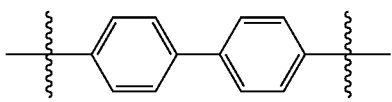

L1

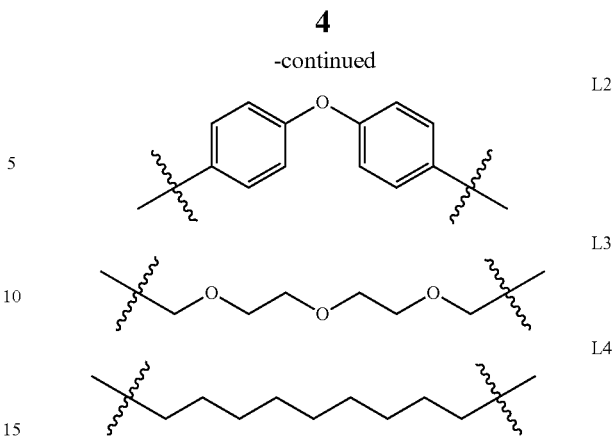

L2

L3

L4

With reference to Formula I, alkyl refers to a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), or pentyl (including all isomeric forms), and the like. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy, and —C(O)O-alkyl.

Inorganic anions include halides ($F^-$, $Cl^-$, $Br^-$, $I^-$), phosphites and phosphates ($PF_6^-$, $H_2PO_2^-$, $H_2PO_4^-$, $PO_3^-$), borates ($BF_4^-$, $BO_2^-$, $BO_3^-$), nitrites and nitrates ($NO_2^-$, $NO_3^-$), sulfates ($HSO_4^-$), cyanide and cyanates ($CN^-$, $SCN^-$, $CNO^-$), dicyanamide (($CN)_2N^-$), azide ($N_3^-$), carbonates ($HCO_3^-$), bromated ($BrO_3^-$), iodates ($IO_3^-$, $IO_4^-$), chlorites and chlorates ($ClO^-$, $ClO_2^-$, $ClO_3^-$, $ClO_4^-$) and metal halide anions such as $ZnCl_3$—, $ZnBr_3^-$, $SnCl_5^-$, $SnBr_5^-$, $FeCl_4^-$, $AuCl_4^-$, $AuBr_4^-$, $GaCl_4^-$, $AlCl_4^-$, $Al_2Cl_7^-$, $Al_3Cl_{10}^-$.

Organic anions include carboxylates, thiocarboxylates, carbamates, dithiocarbamates, xanthates, sulfonates, organo-sulfates, organo-sulfamates, organo-phosphates, phosphonates, acetates, glucanates and thiophosphonates, as well as imides, thioimides, sulfonimides, N-acyl-sulfonamides, and N-acil-phosphoramides, ascorbates, isocyanurates, barbiturates, ferrocenecarboxylates methanefullerenecarboxylates, and mixtures thereof.

In some embodiments, R is a hydrogen or a methyl group. In other embodiments, L is linker L1, L2 or L3. In yet other embodiments X is a halide anion. In particular embodiments, the inhibitor of the invention is one of the following compounds.

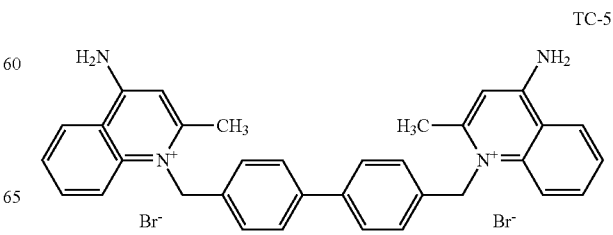

TC-5

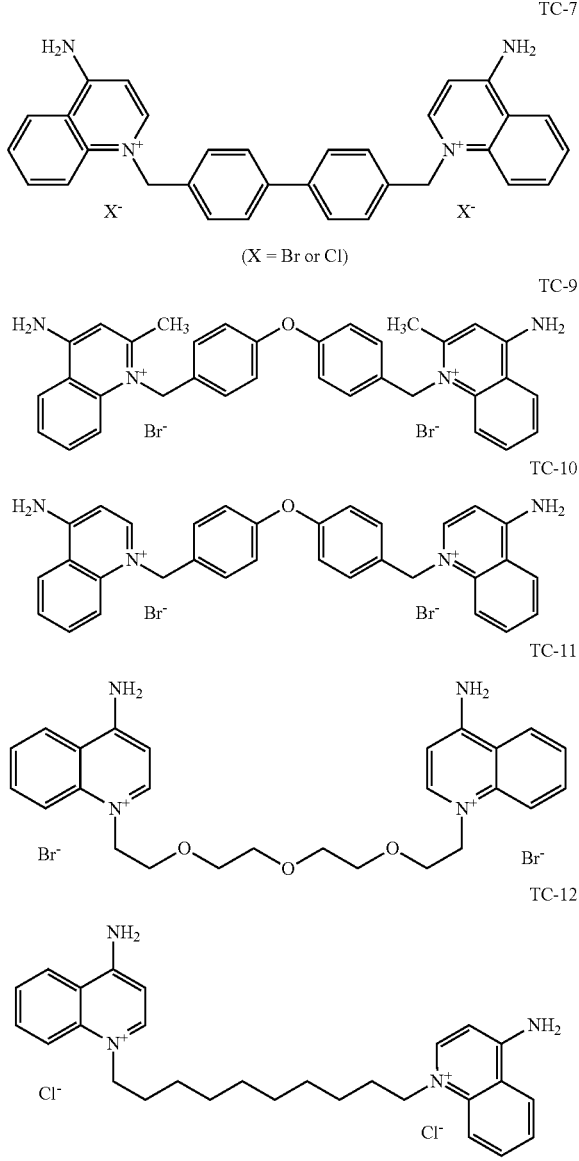

Compounds of the present invention find use in methods for inhibiting the activity of type 4 prepilin peptidases. Although the mechanistic details of pilin N-terminal cleavage and methylation have been characterized most extensively using the *Vibrio cholerae* (TcpJ and VcpD) and *Pseudomonas aeruginosa* (PilD; also called XcpA) prepilin peptidases, the prior art recognizes that homologs of these enzymes are found in all systems with type IV pilin proteins (see, e.g., Carmen, et al. (2012) *Microbiol. Mol. Biol. Rev.* 76:740-772). Indeed, type 4 prepilin peptidases are found in *Vibrio cholera* (TcpJ), *V. vulnificus* (VvpD), *Pseudomonas aeruginosa* (PilD), *P. putida* (PilD), *Neisseria gonorrhoeae* (PilD), *Escherichia coli* (HopD, BfpP), *Bacillus subtilis* (ComC), *Dichelobacter nodosus* (FimP), *Burkholderia pseudomallei* (GspO), *Synechocystis* sp. (HofD), *Haemophilus influenza* (HopD), *Salmonella typhimurium* (HopD), *Erwinia carotovora* (OutO), *E. chrysanthemi* (OutO), *Aquifex aeolicus* (PilD), *Legionella pneumonphilia* (PilD), *Myxococcus xanthus* (PilD), *Chlorobium limicola* (Pph), *Klebsiella pneumoniae* (PulO), *Aeromonas hydrophilia* (TapD), *A. salmonicida* (TapD), and *Xanthomonas campestris* (XpsO). Moreover, alignment of the amino acid sequence of the TFPPs from these organisms indicates that active site $Asp^{125}$ and $Asp^{189}$ residues are present in each of these enzymes (LaPointe & Taylor (2000) *J. Biol. Chem.* 275:1502-10). As such, the compounds of this invention are of use in inhibiting the activity of any type 4 prepilin peptidase.

The inhibitory activity of the compounds of this invention can be demonstrated using any standard type 4 prepilin peptidase in vitro cleavage assay. By way of illustration, the effect of inhibitors on the peptidase activity of TcpJ can be determined by incubating the inhibitor with an amount of membrane preparation known to contain 1 unit of activity of TcpJ for 30 minutes at room temperature. The TcpJ/inhibitor mixture is then tested for peptidase activity. Amounts of cleaved TcpA prepilin can be quantitated and applied to the formula: % cleavage=(amount of cleaved TcpA in inhibition assay/amount of cleaved TcpA in no inhibitor control assay)×100.

Compounds that inhibit type 4 prepilin peptidase cleavage activity are particularly useful as anti-bacterial agents and therefore find application in methods for preventing or treating bacterial infections. The compounds can be administered to inhibit virulence factor production by bacteria and to inhibit bacterial infections in a host subject. Mammals, birds and other animals may be treated by the compounds, compositions or methods described herein. Such mammals and birds include humans, dogs, cats and livestock, such as horses, cattle, sheep, goats, chickens and turkeys and the like. Moreover, plants may also be treated by the compounds, compositions or methods of the invention.

Bacterial infections that can be prevented or treated in accordance with this invention include bacterial known to express type 4 prepilin or prepilin-like proteins and cognate TFPP enzymes. Such bacteria include, but are not limited to, *V. cholera*, *V. vulnificus*, *P. aeruginosa P. putida*, *N. gonorrhoeae*, *E. coli*, *B. subtilis*, *D. nodosus*, *B. pseudomallei*, *Synechocystis* sp., *H. influenza*, *S. typhimurium*, *E. carotovora*, *E. chrysanthemi*, *A. aeolicus*, *L. pneumonphilia*, *M. xanthus*, *C. limicola*, *K. pneumoniae*, *A. hydrophilia*, *A. salmonicida*, and *X. campestris*.

The term "prevention" refers to the inhibition or delay of bacterial infection of a host. Given that type 4 pilin are involved in colonization and pilus formation, and type 4 pilin-like proteins are associated with secretion of toxins and other factors associated with bacterial virulence and destruction of host tissue, inhibition of TFPP activity by the compounds of this invention can block colonization and virulence factor production therefore preventing infection. The term "treatment" refers to the ability of the compounds described herein to impart a benefit to a subject afflicted with a bacterial infection, including an improvement in the condition of the subject or delay in disease progression.

The compound of the invention may also be useful in the treatment or prevention of, inter alfa, wounds, ulcers and lesions for example, cutaneous wounds such cuts or burns, and conditions associated therewith. As used herein "treatment of a wound" may include wound healing and associated conditions and therapy which promotes, augments, or accelerates healing of tissues and includes post-operative scarring, burns, psoriasis, acceleration of tissue remodeling, for example, post cosmetic surgery and organ transplantation.

For prophylactic or therapeutic applications, compounds can be administered in pharmaceutical compositions containing one or more compounds of the invention in admixture with a pharmaceutically acceptable vehicle or carrier. Pharmaceutical compositions containing one or more compounds of the invention can be prepared by procedures known in the art using well-known and readily available ingredients. For example, the compound(s) can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatine, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing one or more of the compounds of the invention can include buffering agents such as calcium carbonate, magnesium oxide and magnesium carbonate. Suitable buffering agents may also include acetic acid in a salt, citric acid in a salt, boric acid in a salt and phosphoric acid in a salt. Caplets and tablets can also include inactive ingredients such as cellulose, pregelatinized starch, silicon dioxide, hydroxyl propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one compound of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more compounds of the invention are designed to resist disintegration in the stomach and dissolve in the more neutral to alkaline environment of the duodenum.

The compounds of the invention can also be formulated as elixirs or solutions for convenient oral administration or as solutions appropriate for parenteral administration, for instance by intramuscular, subcutaneous, intraperitoneal or intravenous routes. The pharmaceutical formulations of the compounds of the invention can also take the form of an aqueous or anhydrous solution or dispersion, or alternatively the form of an emulsion or suspension or salve.

Thus, the compounds may be formulated for parenteral administration (e.g., by injection, for example, bolus injection or continuous infusion) and may be presented in unit dose form in ampoules, pre-filled syringes, small volume infusion containers or in multi-dose containers. As noted above, preservatives can be added to help maintain the shelve life of the dosage form. The active compounds and other ingredients may form suspensions, solutions, or emulsions in oily or aqueous vehicles, and may contain formulatory agents such as suspending, stabilizing and/or dispersing agents. Alternatively, the active compounds and other ingredients may be in powder form, obtained by aseptic isolation of sterile solid or by lyophilization from solution for constitution with a suitable vehicle, e.g., sterile, pyrogen-free water before use.

As indicated, the compounds of this invention can also be used in the treatment of a wound. Thus, in one embodiment of the invention there is provided a substrate to which a compound of the invention is applied or attached. Preferably, the substrate is suitable for application to wounds or delivery to wound sites. Preferably, the substrate allows for the transfer of the compounds of the invention from the substrate to a wound bed to achieve their antibiotic effect. The substrate may be a dressing, for example, wound dressing. The dressing may be composed of a fabric material or it may be a collagen-like material.

The compounds of the invention may also find application as/in a disinfectant. In this context, the compound or pharmaceutical compositions of the invention may be applied, either alone or in combination with other disinfecting agents, to a surface to be treated. As used herein a "surface to be treated" may be a substrate as defined herein or a medical device.

To achieve the desired effect(s), an effective amount of the compound of the invention may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight or at least about 1 mg/kg to about 20 mg/kg of body weight, although other dosages may provide beneficial results. The amount administered will vary depending on various factors including, but not limited to, the compound chosen and its clinical effects, the disease, the weight, the physical condition, the health, the age of the mammal, and whether prevention or treatment is to be achieved. Such factors can be readily determined by the clinician examining the empirical data from the clinical trials and examining the preclinical animal model results or other test systems that are available in the art.

Administration of the compounds of the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the compounds of the invention may be essentially continuous over a pre-selected period of time or may be in a series of spaced doses. Both local and systemic administration is contemplated.

To prepare the composition, compounds are synthesized or otherwise obtained, purified as necessary or desired, and then lyophilized and stabilized. The compounds can then be adjusted to the appropriate concentration and optionally combined with other agents. The absolute weight of a given compounds included in a unit dose can vary widely. For example, about 0.01 to about 2 g or about 0.01 to about 500 mg, of at least one compound of the invention, or a plurality of compounds. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the compounds of the invention can vary as well. Such daily doses can range, for example, from about 0.001 g/day to about 100 or 50 g/day, from about 0.1 g/day to about 25 g/day, from about 0.1 g/day to about 12 g/day, from about 0.1 g/day to about 5 g/day, from about 0.1 g/day to about 2.5 g/day, from about 0.1 g/day to about 2 g/day, from about 0.5 g/day to about 8 g/day, from about 0.5 g/day to about 4 g/day, from about 0.5 g/day to about 2 g/day, and from about 0.5 g/day to about 1 g/day.

Thus, one or more suitable unit dosage forms containing the compounds of the invention can be administered by a variety of routes including oral, parenteral (including subcutaneous, intravenous, intramuscular and intraperitoneal), rectal, dermal, transdermal, intrathoracic, intrapulmonary and intranasal (respiratory) routes. The compounds may also be formulated in a lipid formulation or for sustained release (for example, using microencapsulation, see WO 94/07529, and U.S. Pat. No. 4,962,091). The formulations may, where appropriate, be conveniently presented in discrete unit dosage forms and may be prepared by any of the methods well-known to the pharmaceutical arts. Such methods may include the step of mixing the compounds with liquid carriers, solid matrices, semi-solid carriers, finely divided solid carriers or combinations thereof, and then, if necessary, introducing or shaping the product into the desired delivery system.

In addition to prevention and treatment, it is posited that the compounds of the invention will be useful in inhibiting development of drug resistant strains of bacteria when administered in combination with a second known therapeutically effective anti-bacterial agent. Thus, in some embodiments, it is preferred that the active compound be administered just prior to or at the same time as the second anti-bacterial agent. Accordingly, the present invention also relates to compositions containing a compound which inhibits type 4 prepilin peptidase activity and a second known therapeutically effective anti-bacterial agent.

In yet a further embodiment, it is posited that the compounds of the invention can, like dequalinium and its analogs (Rotenberg, et al. (1990) *Cancer Res.* 50:677-85; Weiss, et al. (1987) *Proc. Natl. Acad. Sci.* 84:5444-8; U.S. Pat. No. 6,974,871), provide protection of human skin from the harmful effects of the sun, as well as inhibiting tumor formation and metastasis.

Example 1: Inhibitor Preparation

Exemplary compounds of this invention were prepared in accordance with Schemes 1-4.

SCHEME 1

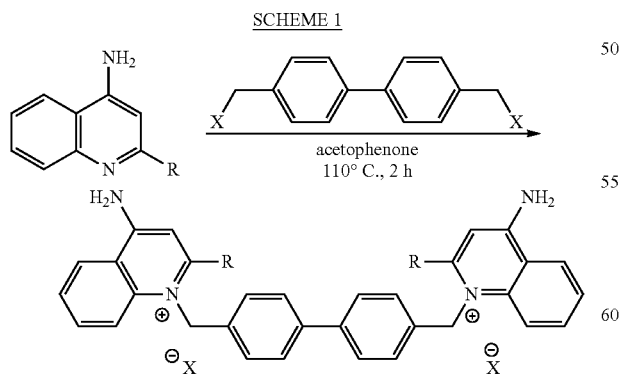

TC-5 R = Me, X = Br, the product is not clean
TC-7 R = H, X = Br, 74%
TC-7 R = H, X = Cl, 65%

SCHEME 2

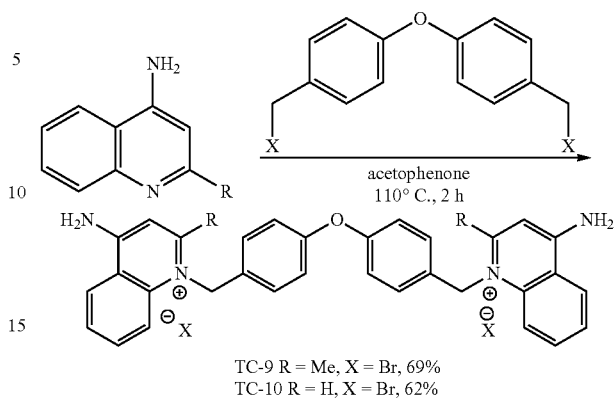

TC-9 R = Me, X = Br, 69%
TC-10 R = H, X = Br, 62%

SCHEME 3

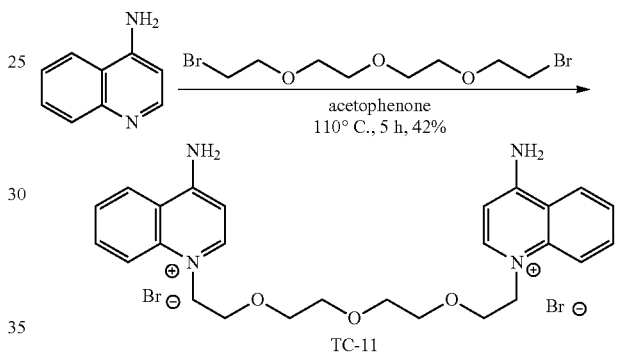

TC-11

SCHEME 4

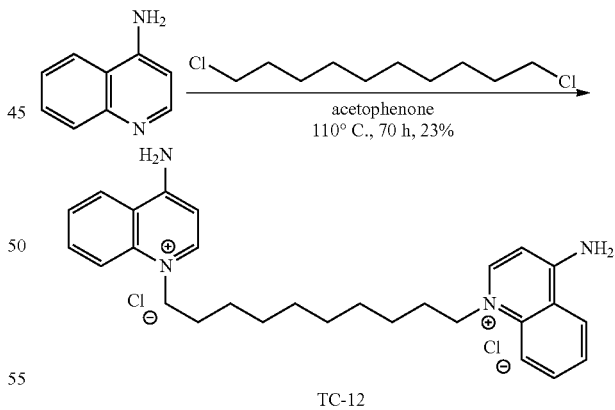

TC-12

Example 2: Membrane Preparations

Membrane preparations were prepared according to a modified cell fractionation protocol (Pfau (1998) *J. Bact.* 180(17):4724-33). Overnight cultures were placed on ice for 20 minutes then pelleted at 5000×g for 10 minutes. The cell pellet was resuspended in 1 ml 200 mM Tris pH 8.0 to which 1 ml 50 mM Tris pH 8.0, 1 M sucrose, 2 ml water, 20 µl 0.5 M EDTA, and 20 µl lysozyme (10 mg/ml) were added. The cell suspension was allowed to incubate on ice for 30 minutes. Then, 100 µl 1 M MgSO$_4$ was added and the suspension was pelleted at 5000×g for 10 minutes. The cell pellet was resuspended in 5 ml 50 mM Tris pH 8.0, sonicated 3 times for 15 seconds, and centrifuged at 5000×g for 10 minutes. The supernatant was then centrifuged at 230,000×g for 15 minutes. The resulting pellet, which contained the total membrane fraction was resuspended in 200 µl 50 mM Tris pH 8.0.

Example 3: In Vitro Cleavage Assay

A membrane preparation from the *E. coli* strain K38 p3Z-A, pGP1-2, which was determined to contain 0.2 µg TcpA prepilin/µl, was the source of prepilin in the in vitro TcpJ proteases assay instead of purified prepilin. A membrane preparation of the TcpJ-expressing strain JM109, pCL9, both wild-type and mutant alleles, was the source of the wild-type and mutant TcpJ protein for the in vitro cleavage reactions. The 100 µl processing reaction is performed by combining a 50 µl substrate fraction with a 50 µl enzyme fraction and incubating at 37° C. for 1 hour. The substrate fraction was prepared by combining 5 µl of the TcpA-containing membrane preparation (1 µg TcpA), 10 µl 0.5% w/v cardiolipin, 20 µl of 2× assay buffer (125 mM triethanolamine HCl pH 7.5, 2.5% v/v TRITON-X-100), and brought up to the total volume with water. The enzyme fraction was prepared by combining varying volumes of TcpJ-containing membrane preparation and water to bring the volume to 50 µl. The cleavage reaction was stopped by the addition of 100 µl of 5× protein sample buffer.

Example 4: Inhibitor Activity

Chemical inhibitors were tested for their ability to prevent cleavage of TcpA from the prepilin form to the mature form in the in vitro cleavage assay. Inhibitors were added at specific concentrations to the in vitro assay mixture, which contained 1 unit of TcpJ activity. Inhibitors were added to both enzyme and substrate fractions so that when combined the inhibitor concentration remained constant. The enzyme fraction was allowed to incubate at room temperature for 30 minutes prior to combination of the two fractions. The 100 µl reaction was allowed to proceed for 1 hour at 37° C. before addition of 100 µl of 2×SDS protein sample buffer that stopped the reaction.

Compounds of the invention were shown to inhibit the activity of TFPP (as indicated by a loss of bacterial clumping at the bottom of cell culture tubes and disappearance of the TcpA pilin band on a western blot). In particular, compound TC-7 was found to have a lower IC$_{50}$ value compared to compounds where R is methyl.

What is claimed is:

1. A compound having the structure of Formula I:

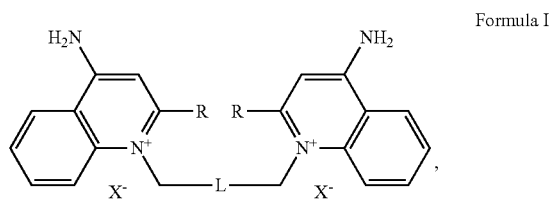

Formula I wherein R is a hydrogen or unsubstituted C$_1$-C$_6$ alkyl group, X is an organic or inorganic anion, and L is a linker having one of the following structures:

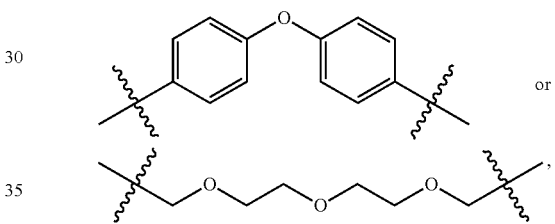

2. A pharmaceutical composition comprising the compound of claim 1 in admixture with a pharmaceutically acceptable carrier.

* * * * *

UNITED STATES PATENT AND TRADEMARK OFFICE
CERTIFICATE OF CORRECTION

PATENT NO. : 9,796,679 B2
APPLICATION NO. : 15/117940
DATED : October 24, 2017
INVENTOR(S) : Ronald K. Taylor and Gordon W. Gribble Page 1 of 1

It is certified that error appears in the above-identified patent and that said Letters Patent is hereby corrected as shown below:

In the Specification

At Column 1, please delete Lines 10-12 and insert in its place the following:
--This invention was made with government support under grant number AI025096 awarded by the National Institutes of Health. The government has certain rights in the invention.--

Signed and Sealed this
Fifteenth Day of September, 2020

Andrei Iancu
*Director of the United States Patent and Trademark Office*